US00PP34214P2

(12) United States Plant Patent
Pounders, Jr.

(10) Patent No.: US PP34,214 P2
(45) Date of Patent: May 10, 2022

(54) ***VITEX* PLANT NAMED 'JBG 19002'**

(50) Latin Name: *Vitex agnus-castus*
Varietal Denomination: JBG 19002

(71) Applicant: Innovative Plants LLC, Decatur, AL (US)

(72) Inventor: Cecil T. Pounders, Jr., Decatur, AL (US)

(73) Assignee: Innovative Plants LLC, Decatur, AL (US)

( * ) Notice: Subject to any disclaimer, the term of this patent is extended or adjusted under 35 U.S.C. 154(b) by 0 days.

(21) Appl. No.: 17/498,117

(22) Filed: Oct. 11, 2021

(51) Int. Cl.
*A01H 5/00* (2018.01)
*A01H 6/50* (2018.01)

(52) U.S. Cl.
USPC ..... Plt./226
CPC ..... *A01H 6/50* (2018.05)

(58) Field of Classification Search
USPC ..... Plt./226
CPC ..... A01H 5/02; A01H 5/00
See application file for complete search history.

*Primary Examiner* — Kent L Bell
(74) *Attorney, Agent, or Firm* — Weatherly IP Solutions, LLC; Barbara Campbell

(57) ABSTRACT

A new and distinct cultivar of *Vitex* named 'JBG 19002' that is characterized by an upright vase-shaped habit, compound palmate leaves consisting of five narrow leaflets and saturated mid-dark violet-blue flowers from late spring through late summer, is disclosed.

2 Drawing Sheets

Genus and species: *Vitex agnus-castus.*
Variety denomination: 'JBG 19002'.

BACKGROUND

The present invention relates to a new variety of chaste tree, a perennial shrub grown for use in borders, landscape, and as a specimen plant. The new invention from the family Lamiaceae is known botanically as *Vitex agnus-castus* and will be referred to hereinafter by the cultivar name 'JBG 19002'.

The inventor commenced his *Vitex* breeding program in Decatur, Ala. in 2015 with the objective of developing dwarf plant forms with an extended period of flowering, in a variety of flower colors. 'JBG 19002' was selected in 2018 as a single seedling from amongst approximately 500 seedlings which the inventor had raised from seed collected from an open-pollinated *Vitex* plant named 'PIIVAC-II' (U.S. Plant Pat. No. 26,775).

The distinguishing traits of 'JBG 19002' are upright vase-shaped plant habit, compound palmate leaves with five narrow leaflets, and a prolific display of mid-dark violet-blue flowers that bloom from late spring through late summer. In a 3.7-gallon container, 'JBG 19002' grows to 60 cm. in height (including the flowers) and 70 cm. in width The first asexual reproduction of 'JBG 19002' was conducted at the inventor's nursery in summer 2018. The method used was softwood cuttings, rooted under mist. Since that time, under careful observation 'JBG 19002' has been determined fixed, stable and true to type in subsequent generations of asexual propagation.

SUMMARY

The following traits have been repeatedly observed and represent the distinguishing characteristics of 'JBG 19002'. These traits in combination distinguish 'JBG 19002' from all other existing varieties of *Vitex* known to the inventor. 'JBG 19002' has not been tested under all possible conditions. Phenotypic differences may be observed with variations in environmental, climatic, and cultural conditions without however any variance in genotype.

1. 'JBG 19002' exhibits upright vase-shaped habit.
2. 'JBG 19002' bears compound palmate leaves consisting of five narrow leaflets.
3. 'JBG 19002' saturated mid-dark violet-blue flowers from late spring through late summer.
4. When grown in a large (i.e., 3.7-gallon) container, a flowering plant of 'JBG 19002' reaches 60 cm in height and 70 cm in diameter.
5. 'JBG 19002' is hardy to USDA Zone 6.

DESCRIPTION OF THE PHOTOGRAPHS

The accompanying color photographs illustrate the overall appearance of 'JBG 19002' showing its colors as true as is reasonably possible to obtain in color reproductions of this type. The photographs were made from a fifteen-month-old plant which has been grown outdoors in a 3.7-gallon container in Oxnard, Calif. Colors in the photographs may differ from color values cited in the detailed botanical description, which accurately describe the actual color of 'JBG 19002'.

Figure 1:
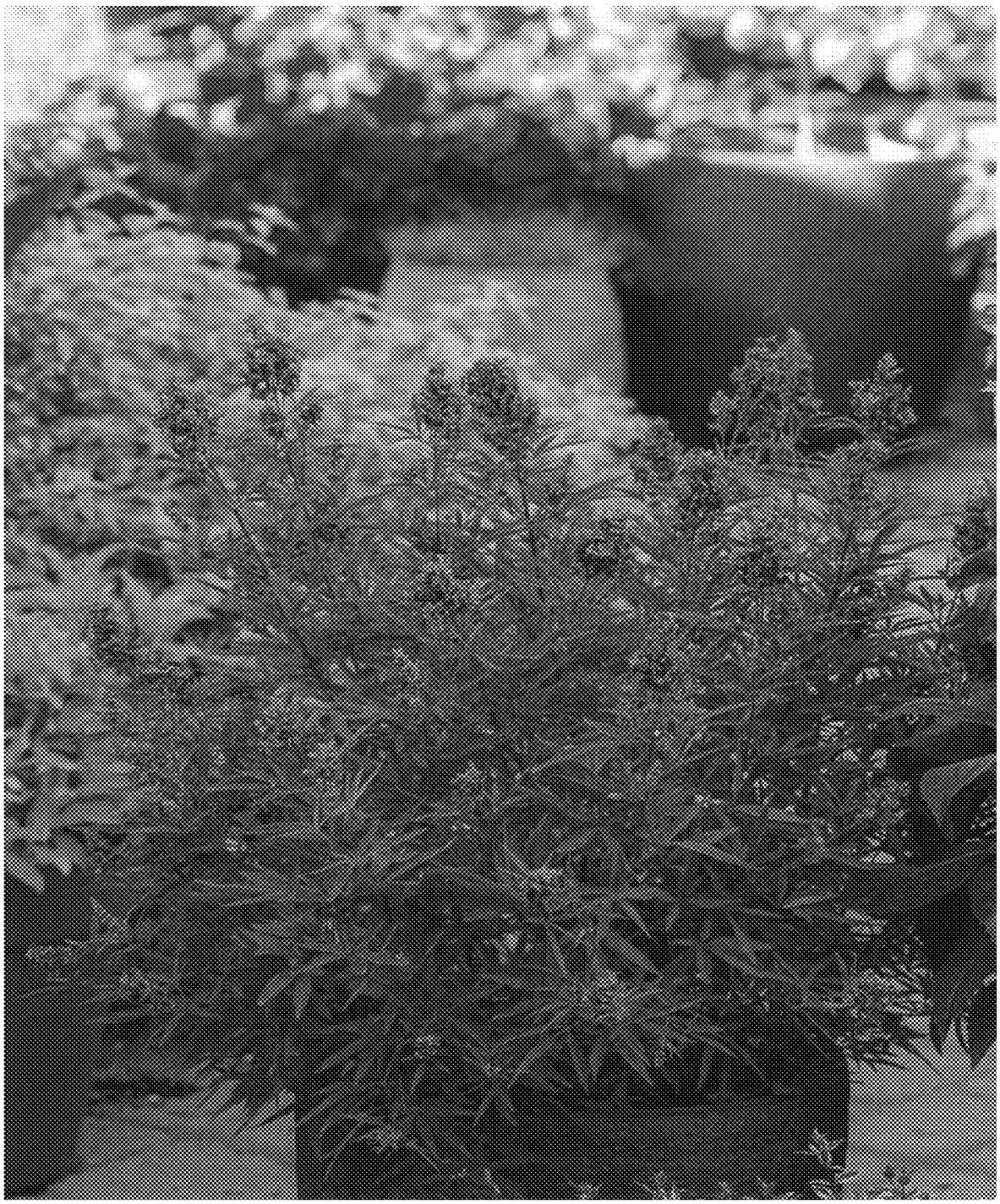

FIG. 1 depicts a whole plant of 'JBG 19002' at peak flowering in the first week of August.

Figure 2:
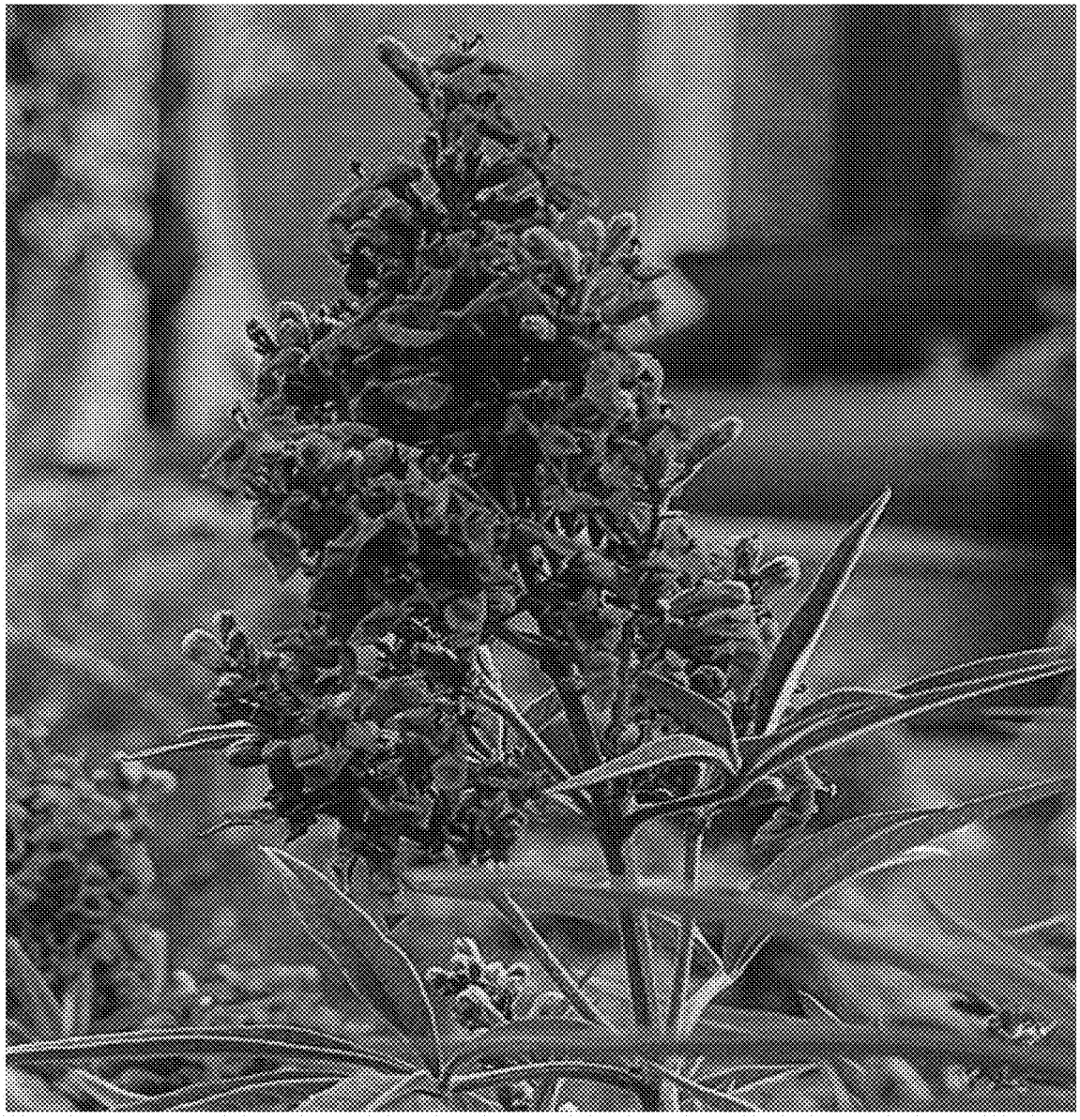

FIG. 2 presents a close-up view of the inflorescence and flowers of 'JBG 19002' during peak flowering in early August.

BOTANICAL DESCRIPTION OF THE NEW VARIETY

The following is a detailed botanical description of 'JBG 19002'. Observations and measurements were collected in late August from a 3.7-gallon container-grown plant which was growing in Oxnard, Calif. out of doors. Color determinations are made in accordance with the 2007 Fifth Edition of The Royal Horticultural Society Colour Chart from London, England, except where general color terms of ordinary dictionary significance are used.

Plant:

*Botanical classification.*—*Vitex agnus-castus.*

*Family.*—Lamiaceae.

*Genus.*—*Vitex.*

*Species.*—*agnus-castus.*

*Denomination.*—'JBG 19002'.

*Common name.*—Chaste Tree.

*Habit.*—Upright, vase-shaped.

*Commercial category.*—Perennial shrub.

*Use.*—Suitable for border, landscape, and container grown specimen plant.

*Suggested commercial container sizes* (*flowering plants*).—1-gallon, 2-gallons, 3-gallons and larger.

Parentage: Seed collected from open-pollinated *Vitex agnus-castus* 'PIIVAC-II' (U.S. Plant Pat. No. 26,775).

Propagation and growth:

*Propagation method.*—Softwood cuttings rooted under mist.

*Rooting system.*—Generally coarse with finer adventitious roots, color 165C.

*Vigor.*—Moderate.

*Crop time.*—4 weeks to produce a rooted cutting, 4 to 6 weeks to produce a 2-inch liner young plant from a rooted cutting, and a further 4 to 5 months to produce a flowering 1-gallon or 2-gallon container. Larger specimen plants (3-gallon containers and larger) require an additional season of growth.

*Plant height* (*including inflorescences*).—60 cm.

*Plant width.*—70 cm.

*Cultural requirements.*—Performs best in full sun and requires light to moderate watering.

*Drought tolerance.*—High.

*Hardiness.*—USDA Zone 6.

Stem, branches:

*Branching habit.*—Basal stems (5 observed), primary lateral branches (20 to 25 observed), and secondary branches (40 to 50 observed).

*Stem shape.*—Cylindrical.

*Stem surface.*—Coriaceous with lighter longitudinal ridges, except youngest growth smoother and very lightly pubescent.

*Stem appearance.*—Matte.

*Color.*—197B, longitudinal ridges 198D.

*Stem length* (*unstopped*).—50 cm.

*Stem diameter* (*maximum, at base*).—18 mm.

*Stem strength.*—Very strong and woody except newer growth stiff and wiry.

*Primary branches.*—5 to 6 opposite pairs arranged along stem at intervals of 8 cm to 10 cm.

*Secondary branches.*—Terminal axillary shoots arranged in opposite pairs at each primary branch node.

*Branch stem shape.*—Cylindrical.

*Branch stem surface.*—Lightly pubescent; very short fine white hairs, color NN155D.

*Branch stem color.*—As stem 197B except young growth 164B.

Foliage:

*Type.*—Deciduous.

*Leaf arrangement.*—Opposite pairs.

*Leaf type.*—Compound palmate, 5 leaflets.

*Leaf division* (*leaflets*).—Simple.

*Leaflet quantity.*—5 to 6 pairs per primary branch, 1 pair per secondary branch.

*Leaflet margin.*—Smooth, entire.

*Leaflet surface* (*adaxial surface*).—Glabrous, semi-glossy.

*Leaflet surface* (*abaxial surface*).—Glabrous, matte.

*Leaflet shape.*—Narrowly lanceolate.

*Leaf dimensions* (*compound leaf*).—65 mm in length, 60 mm in width.

*Leaflet length.*—65 mm (central leaflet), 45 mm to 50 mm (first pair of leaflets), 30 mm. (second, outermost pair of leaflets).

*Leaflet width.*—12 mm (central leaflet), 8 mm (first pair of leaflets), 5 mm. (second, outermost pair of leaflets).

*Leaflet color* (*adaxial surface*).—N137B.

*Leaflet color* (*adaxial surface*).—191A.

*Venation pattern.*—Pinnate.

*Vein color* (*adaxial surface*).—As leaf N137B. Veins only visible as slight depressions.

*Vein color* (*abaxial surface*).—193A.

*Leaflet apex.*—Acute.

*Leaflet base.*—Cuneate.

*Attachment.*—Petiolate.

*Petiole surface.*—Lightly pubescent; very short fine white hairs, color NN155D.

*Petiole shape.*—Sulcate.

*Petiole color.*—Ranges between 164A and 164B.

*Petiole dimensions.*—20 mm to 24 mm. in length, 1.5 mm. in diameter.

Inflorescence:

*Type.*—Compound cyme with terminal and axillary cymes.

*Inflorescence quantity.*—70 to 80 per 3.7-gallon container plant.

*Inflorescence: dimensions* (*terminal cymes*).—55 mm in length, 35 mm in width.

*Inflorescence: dimensions* (*axillary cymes*).—40 mm in length, 18 mm in width.

*Rate of opening.*—Approximately 10 days for each inflorescence to open entirely.

*Blooming months.*—June through September.

*Flower quantity.*—100 to 120 per terminal cyme, 25 to 35 per axillary cyme.

*Flower dimensions.*—7 mm in height, 5 mm in width.

*Flower aspect.*—Upright.

*Persistent or self-cleaning.*—Mostly persistent.

*Peduncle shape.*—Cylindrical.

*Peduncle surface.*—Lightly pubescent; very short fine white hairs, color NN155D.

*Peduncle strength.*—Moderate.

*Peduncle color.*—164B.

*Peduncle length.*—15 mm to 23 mm (terminal cymes), 12 mm to 15 mm. (axillary cymes).

*Peduncle diameter.*—2 mm (terminal cymes), 1.5 mm (axillary cymes).

*Pedicel dimensions.*—2 mm to 4 mm in length and less than 1 mm in diameter.

*Pedicel color.*—191C.

*Pedicel strength.*—Weak, easily dislodged from peduncle.

*Bud quantity.*—70 to 80 per inflorescence.

*Bud shape.*—Globular.

*Bud color.*—Ranges between 85C and 85B.
*Bud surface.*—Tomentose, with very fine hairs, less than 1 mm. in length, color closest to NN155D.
*Bud dimensions.*—3 mm. in diameter.
*Corolla shape.*—Campanulate with 5 petaloid lobes.
*Corolla dimensions.*—4 mm in depth and 1.5 mm in diameter.
*Corolla tube dimensions.*—2 mm in length and 1 mm in diameter.
*Corolla tube color.*—Ranges between 85D and 91D.
*Corolla lobes.*—5 petaloid lobes of which 2 are upper, basally fused, and 3 lower, longitudinally fused to form a lower lip.
*Lobe color* (*both surfaces*).—93C when newly opened, darker N89B to N89C when fully open and at peak flowering.
*Lobe margin.*—Smooth, entire.
*Lobe shape.*—Upper lobes obovate, lower lobes spathulate.
*Lobe apex.*—Obtuse.
*Calyx shape.*—Campanulate.
*Calyx color* (*both surfaces*).—145C (flowers present), 182D (after flowering).
*Calyx dimensions.*—3 mm in length and 2 mm in diameter.
*Sepals.*—5 in number, basally and longitudinally fused, apex free.
*Sepal shape.*—Narrow elliptic.
*Sepal dimensions.*—3 mm. in length and 1 mm. in width.
*Sepal color* (*both surfaces*).—145C (flowers present), 182D (after flowering).
*Sepal margin.*—Entire.
*Sepal apex.*—Acute.
*Sepal surface.*—Lightly pubescent; very short fine white hairs, color NN155D.
*Flower fragrance.*—None observed.

Reproductive organs:
*Stamen quantity.*—4 in number.
*Stamen dimensions.*—5 mm in length, 0.25 mm in diameter.
*Stamen color.*—85D.
*Anthers.*—Bilobed, Dorsifixed, 1.5 mm in length, 0.75 mm in width.
*Pollen color.*—93A.
*Pistil.*—1, filamentose.
*Pistil dimensions.*—4 mm in length, 0.2 mm in diameter.
*Stigma.*—Absent or not discernable.
*Ovary position.*—Superior.
*Ovary shape.*—Flattened sphere.
*Ovary dimensions.*—2.5 mm in diameter.
*Ovary color.*—145B.
*Ovary surface.*—Glabrous.
Seed: Sparse, shape ovoid, 1 mm in length, 0.75 mm in diameter, color black 203A.
Disease and pest resistance or susceptibility: None. The genus *Vitex* is generally resistant to plant pests and diseases.

COMPARISON WITH PARENTAL LINES AND KNOWN VARIETY

The closest comparison plant known to the inventor is the seed parent variety and commercial line *Vitex* plant named 'PIIVAC-II' (U.S. Plant Pat. No. 26,775). In comparison with 'PIIVAC-II', 'JBG 19002' bears shorter and narrower leaves and leaflets, smaller inflorescences, and flowers which are darker violet-blue in color.

I claim:

1. A new and distinct cultivar of *Vitex* plant named 'JBG 19002' as described and illustrated herein.

* * * * *